(12) United States Patent
Gibson

(10) Patent No.: US 7,571,012 B2
(45) Date of Patent: Aug. 4, 2009

(54) APPARATUS FOR DELIVERY OF PHARMACEUTICALS TO THE COCHLEA

(75) Inventor: Peter Gibson, Lane Cove (AU)

(73) Assignee: Cochlear Limited, Lane Cove (AU)

( * ) Notice: Subject to any disclaimer, the term of this patent is extended or adjusted under 35 U.S.C. 154(b) by 344 days.

(21) Appl. No.: 10/416,634

(22) PCT Filed: Nov. 14, 2001

(86) PCT No.: PCT/AU01/01479

§ 371 (c)(1), (2), (4) Date: Nov. 10, 2003

(87) PCT Pub. No.: WO02/41666

PCT Pub. Date: May 23, 2002

(65) Prior Publication Data

US 2004/0078057 A1   Apr. 22, 2004

(30) Foreign Application Priority Data

Nov. 14, 2000 (AU) .................................... PR1484

(51) Int. Cl.
*A61F 11/04* (2006.01)
*A61N 1/04* (2006.01)
*A61M 25/01* (2006.01)

(52) U.S. Cl. .......................... 607/137; 607/3; 604/244; 604/256; 604/265; 604/528

(58) Field of Classification Search ............. 607/55–57, 607/120, 136–137, 1–3; 604/256, 890.1, 604/891.1, 11–15, 19–21, 164.01, 164.02, 604/164.05, 164.08, 164.09, 164.12, 164.13, 604/165.01–165.04, 167.01–167.06, 170.01–170.03, 604/171, 172, 93.01, 244, 48, 246, 263–265, 604/500, 514; 600/25, 379; 623/10, 23.64, 623/23.68, 23.75, 24–25; 606/32, 34, 41, 606/108–109, 129

See application file for complete search history.

(56) References Cited

U.S. PATENT DOCUMENTS 4,306,563 A * 12/1981 Iwatschenko ............... 604/265

(Continued)

FOREIGN PATENT DOCUMENTS

DE   100 320 000 A1   1/2001

(Continued)

OTHER PUBLICATIONS

International Search Report dated Nov. 29, 2001; corresponding PCT/AU01/01479 filed Dec. 3, 2001 published as WO 02/41666 on May 23, 2002; Applicant: Cochlear Limited; Inventors: Peter Gibson.

(Continued)

*Primary Examiner*—Carl H Layno
*Assistant Examiner*—Jessica Reidel
(74) *Attorney, Agent, or Firm*—Connolly Bove Lodge & Hutz LLP

(57) ABSTRACT

An implantable tissue-stimulating device, such as a cochlear implant, having a resiliently flexible elongate member (11) having a plurality of electrodes (12) positioned thereon. The elongate member (11) provides a means of delivering at least one bio-active substance to the implantee following implantation of the elongate member (11). The delivery means can comprise a lumen 21 containing the bio-active substance in a liquid form. The bio-active substance can comprise a steroid or can perform a function of reducing the resting neuron potential of neurons within the cochlea.

40 Claims, 3 Drawing Sheets

U.S. PATENT DOCUMENTS

| | | | |
|---|---|---|---|
| 4,351,337 A | | 9/1982 | Sidman |
| 4,357,497 A | * | 11/1982 | Hochmair et al. ............... 607/5 |
| 4,532,930 A | | 8/1985 | Crosby et al. |
| 4,819,662 A | * | 4/1989 | Heil et al. .................... 607/116 |
| 4,994,069 A | * | 2/1991 | Ritchart et al. .............. 606/191 |
| 5,066,278 A | * | 11/1991 | Hirschberg et al. ......... 604/256 |
| 5,458,631 A | * | 10/1995 | Xavier ........................ 607/117 |
| 5,474,542 A | * | 12/1995 | Gandi et al. ................. 604/265 |
| 5,531,780 A | | 7/1996 | Vachon |
| 5,554,114 A | * | 9/1996 | Wallace et al. .............. 604/508 |
| 5,653,742 A | * | 8/1997 | Parker et al. ................. 607/137 |
| 5,697,951 A | | 12/1997 | Harpstead et al. |
| 5,929,041 A | | 7/1999 | Magal |
| 5,975,085 A | | 11/1999 | Rise |
| 6,038,482 A | * | 3/2000 | Vachon ........................ 607/120 |
| 6,038,484 A | | 3/2000 | Kuzma |
| 6,078,841 A | | 6/2000 | Kuzma |
| 6,125,302 A | | 9/2000 | Kuzma |
| 6,163,729 A | | 12/2000 | Kuzma |
| 6,259,951 B1 | * | 7/2001 | Kuzma et al. .................. 607/57 |
| 6,304,787 B1 | | 10/2001 | Kuzma et al. |
| 6,309,410 B1 | | 10/2001 | Kuzma et al. |
| 6,398,758 B1 | * | 6/2002 | Jacobsen et al. ............ 604/104 |
| 6,421,569 B1 | | 7/2002 | Treaba et al. |
| 7,272,449 B2 | * | 9/2007 | Dadd et al. .................. 607/137 |
| 2002/0077685 A1 | * | 6/2002 | Sundquist et al. ........... 607/116 |
| 2003/0097121 A1 | * | 5/2003 | Jolly et al. ............... 604/891.1 |

FOREIGN PATENT DOCUMENTS

| | | |
|---|---|---|
| DE | 10032000 | 1/2001 |
| EP | 0 007 157 A2 | 1/1980 |
| EP | 0 706 807 A2 | 4/1996 |
| EP | 01 99 4538 | 5/2005 |
| JP | 55-190 | 5/1980 |
| JP | 8-229137 | 9/1996 |
| WO | 96/15665 | 5/1996 |
| WO | 97/10784 | 3/1997 |
| WO | WO 97/10784 | 3/1997 |
| WO | WO 99/00067 | 1/1999 |
| WO | 9911321 | 3/1999 |
| WO | WO 99/55360 | 11/1999 |
| WO | WO 99/55360 A1 | 11/1999 |
| WO | WO/00/57949 | 3/2000 |
| WO | 00/56399 | 9/2000 |
| WO | WO 00/71063 | 11/2000 |
| WO | WO/01/41674 | 6/2001 |
| WO | WO 02/32498 A1 | 4/2002 |
| WO | WO 02/04166 | 5/2002 |
| WO | WO 02/41666 A1 | 5/2002 |
| WO | WO/02/083234 | 10/2002 |
| WO | WO/03/049658 | 6/2003 |
| WO | WO 03/072193 | 9/2003 |

OTHER PUBLICATIONS

Written Opinion dated Jan. 28, 2002; corresponding PCT/AU01/01479 filed Dec. 3, 2001 published as WO 02/41666 on May 23, 2002; Applicant: Cochlear Limited; Inventors: Peter Gibson.

International Preliminary Examination Report dated Oct. 4, 2002; corresponding PCT/AU01/01479 filed Dec. 3, 2001 published as WO 02/41666 02/41666 on May 23, 2002; Applicant: Cochlear Limited; Inventors: Peter Gibson.

Altschuler, et al., "Rescue and Regrowth of Sensory Nerves Following Deafferentation by Neurotrophic Factors," *Annals New York Academy of Sciences*.

Supplementary European Search Report for EP 01 99 4538, dated May 27, 2005.

International Preliminary Examination Report for PCT/AU01/01479.

Notice of Reason(s) for Rejection, Japanese Patent Application No. P2002-543261, Jan. 9, 2007.

Australian Examination Report. Patent Application No. 2007202203. Mailed Oct. 22, 2008.

* cited by examiner

APPARATUS FOR DELIVERY OF PHARMACEUTICALS TO THE COCHLEA

FIELD OF THE INVENTION

The present invention relates to an implantable device and, in particular, to an implantable cochlear electrode assembly.

BACKGROUND OF THE INVENTION

Hearing loss, which may be due to many different causes, is generally of two types, conductive and sensorineural. Of these types, conductive hearing loss occurs where the normal mechanical pathways for sound to reach the hair cells in the cochlea are impeded, for example, by damage to the ossicles. Conductive hearing loss may often be helped by use of conventional hearing aid systems, which amplify sound so that acoustic information does reach the cochlea and the hair cells.

In many people who are profoundly deaf, however, the reason for deafness is sensorineural hearing loss. This type of hearing loss is due to the absence of, or destruction of, the hair cells in the cochlea which transduce acoustic signals into nerve impulses. These people are thus unable to derive suitable benefit from conventional hearing aid systems, because there is damage to or absence of the mechanism for nerve impulses to be generated from sound in the normal manner.

It is for this purpose that cochlear implant systems have been developed. Such systems bypass the hair cells in the cochlea and directly deliver electrical stimulation to the auditory nerve fibres, thereby allowing the brain to perceive a hearing sensation resembling the natural hearing sensation normally delivered to the auditory nerve. U.S. Pat. No. 4,532,930, the contents of which are incorporated herein by reference, provides a description of one type of traditional cochlear implant system.

Cochlear implant systems have typically consisted of two key components, namely an external component commonly referred to as a processor unit, and an implanted internal component commonly referred to as a stimulator/receiver unit. Traditionally, both of these components have cooperated together to provide the sound sensation to an implantee.

The external component has traditionally consisted of a microphone for detecting sounds, such as speech and environmental sounds, a speech processor that converts the detected sounds and particularly speech into a coded signal, a power source such as a battery, and an external antenna transmitter coil.

The coded signal output by the speech processor is transmitted transcutaneously to the implanted stimulator/receiver unit situated within a recess of the temporal bone of the implantee. This transcutaneous transmission occurs through use of an inductive coupling provided between the external antenna transmitter coil which is positioned to communicate with an implanted antenna receiver coil provided with the stimulator/receiver unit. This communication serves two essential purposes, firstly to transcutaneously transmit the coded sound signal and secondly to provide power to the implanted stimulator/receiver unit. Conventionally, this link has been in the form of a radio frequency (RF) link, but other such links have been proposed and implemented with varying degrees of success.

The implanted stimulator/receiver unit typically includes the antenna receiver coil that receives the coded signal and power from the external processor component, and a stimulator that processes the coded signal and outputs a stimulation signal to an intracochlea electrode assembly which applies the electrical stimulation directly to the auditory nerve producing a hearing sensation corresponding to the original detected sound.

The external componentry of the cochlear implant has been traditionally carried on the body of the implantee, such as in a pocket of the implantee's clothing, a belt pouch or in a harness, while the microphone has been mounted on a clip mounted behind the ear or on a clothing lapel of the implantee.

More recently, due in the main to improvements in technology, the physical dimensions of the speech processor have been able to be reduced allowing for the external componentry to be housed in a small unit capable of being worn behind the ear of the implantee. This unit has allowed the microphone, power unit and the speech processor to be housed in a single unit capable of being discretely worn behind the ear, with the external transmitter coil still positioned on the side of the user's head to allow for the transmission of the coded sound signal from the speech processor and power to the implanted stimulator unit. It is also considered that with continued improvements in technology, it may become possible to provide a system whereby all components of the system are implanted inside the head of the implantee resulting in a system that is completely invisible and does not require any external components to operate, at least for a portion of the time.

Together with improvements in available technology much research has been undertaken in the area of understanding the way sound is naturally processed by the human auditory system. With such an increased understanding of how the cochlea naturally processes sounds of varying frequency and magnitude, there is a need to provide an improved cochlear implant system that delivers electrical stimulation to the auditory nerve in a way that takes into account the natural characteristics of the cochlea.

It is known in the art that the cochlea is tonotopically mapped. In other words, the cochlea can be partitioned into regions, with each region being responsive to signals in a particular frequency range. This property of the cochlea is exploited by providing the electrode assembly with an array of electrodes, each electrode being arranged and constructed to deliver a cochlea stimulating signal within a preselected frequency range to the appropriate cochlea region. The electrical currents and electric fields from each electrode stimulate the cilia disposed on the modiola of the cochlea. Several electrodes may be active simultaneously.

It has been found that in order for these electrodes to be effective, the magnitude of the currents flowing from these electrodes and the intensity of the corresponding electric fields, are a function of the distance between the electrodes and the modiola. If this distance is relatively great, the threshold current magnitude must be larger than if the distance is relatively small. Moreover, the current from each electrode may flow in all directions, and the electrical fields corresponding to adjacent electrodes may overlap, thereby causing cross-electrode interference. In order to reduce the threshold stimulation amplitude and to eliminate cross-electrode interference, it is advisable to keep the distance between the electrode array and the modiola as small as possible. This is best accomplished by providing the electrode array in the shape which generally follows the shape of the modiola. Also, this way the delivery of the electrical stimulation to the auditory nerve is most effective as the electrode contacts are as close to the auditory nerves that are particularly responsive to selected pitches of sound waves.

In order to achieve this electrode array position close to the inside wall of the cochlea, the electrode needs to be designed in such a way that it assumes this position upon or immediately following insertion into the cochlea. This is a challenge as the array needs to be shaped such that it assumes a curved shape to conform with the shape of the modiola and must also be shaped such that the insertion process causes minimal trauma to the sensitive structures of the cochlea. In this sense it has been found to be desirable for the electrode array be generally straight during the insertion procedure.

Several procedures have been adopted to provide an electrode assembly that is relatively straightforward to insert while adopting a curved configuration following insertion in the cochlea. In one case, a platinum wire stylet is used to hold a pre-curved electrode array in a generally straight configuration up until insertion. Following insertion, the platinum stylet is withdrawn allowing the array to return to its pre-curved configuration.

In developing electrode array designs, it is of great importance that the design be constructed to minimise potential damage to sensitive structures in the cochlea upon insertion and placement of the array. While electrode arrays are preferably designed to minimise such damage, the cochlea does suffer a degree of trauma due to the insertion process.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

SUMMARY OF THE INVENTION

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

It is a preferred feature of the present invention to provide an electrode assembly that is adapted to assist the cochlea in its recovery from trauma following the insertion of an electrode assembly therein. The present invention is equally applicable to conventional electrode assemblies and electrode assemblies which are designed to conform with the inner wall of the cochlea.

According to a first aspect, the present invention is an implantable tissue-stimulating device comprising:

a resiliently flexible elongate member having a plurality of electrodes mounted thereon; and a bio-active substance delivery means adapted to deliver at least one bio-active substance to the implantee following implantation of the device.

In a preferred embodiment of this invention, the device is a cochlear implant electrode assembly.

In one embodiment, the substance delivery means can comprise at least a portion of the elongate member that has been impregnated with a bio-active substance that can leach therefrom following implantation.

In a further embodiment, the elongate member preferably has a first end that is firstly inserted into the implantee.

In another embodiment, the substance delivery means can include a lumen extending through the elongate member for at least a portion of its length. The lumen can be cylindrical or have any other suitable cross-sectional shape. In one embodiment, the lumen extends through the elongate member for a substantial portion of its length. In a further embodiment, the lumen extends from an opening distal the first end to a position that is at or adjacent the first end. The distal opening of the lumen preferably can be closed by a closure means adapted to seal the opening of the lumen.

The closure means can comprise a plug adapted to be inserted into the lumen and to form a seal therewith. The plug can have a frusto-conical outer wall adapted to seal with the wall of the lumen on insertion. The plug in this embodiment can be formed from a resiliently flexible material such as silicone or polyurethane. Alternatively, the plug could be of any suitable shape and could also be formed from a stiff plastic, such as polytetrafluoroethylene (PTFE), or a metal, such as platinum or stainless steel.

In another embodiment, the closure means can comprise a cap adapted to seal the distal opening of the lumen. In one embodiment, the cap can have a top adapted to seal the opening and a skirt depending therefrom. The skirt can have an engagement means formed on an outer surface thereof adapted to engage with the inner surface of the lumen on mounting of the cap to the lumen. In this embodiment, the inner surface of the lumen can have an engagement means complementary to that on the outer surface of the skirt of the cap. The engagement means on the skirt can comprise a screw thread adapted to engage with a corresponding screw thread on the inner cylindrical surface of the lumen.

The lumen in the elongate member can act as a reservoir for a bio-active substance within the elongate member. In one embodiment, the bio-active substance in the reservoir can leach from the lumen into the surrounding material of the elongate member and eventually migrate to an outer surface of the member that is preferably close to the desired site of action for the bio-active substance. In another embodiment, the elongate member can have one or more substance egress means whereby the substance can move out of the lumen and the elongate member to a position that is preferably close to the desired site of action for the bio-active substance.

Where the bio-active substance is carried in or comprises a fluid, each substance egress means preferably comprises a fluid egress means.

Each fluid egress means preferably has a valve means that allows fluid to exit the lumen but prevents, or at least substantially prevents, fluid flow from external the elongate member back into the lumen within the elongate member.

In a further embodiment, the distal opening of the lumen can be in fluid communication with an additional reservoir for the bio-active substance that is external to the elongate member. A pumping means, such as an osmotic pump, can transfer the bio-active substance from the additional reservoir into the lumen of the elongate member for subsequent delivery to the appropriate site of action.

It is also envisaged that the bio-active substance can be captured in the form of a solid pellet 55. In one embodiment shown in FIG. 5, the solid pellet 55 can be formed by impregnating the bio-active substance in a ceramic or a polymer pellet that has a predetermined rate of release of the bioactive substance. This solid pellet 55 can then be stored in the lumen reservoir or in an external reservoir connectable to the lumen.

In one embodiment, the bioactive substance can comprise a steroid. In another embodiment, the bioactive substance can perform a function of reducing the resting neuron potential of neurons within the cochlea. The use of such substances can result in less energy being required to excite the neurons and cause stimulation.

In a further embodiment, the elongate member can have a first configuration selected to allow said member to be inserted into an implantee's body, such as the cochlea, and a second configuration wherein said elongate member is adapted to apply a preselected tissue stimulation with the electrodes. In a further embodiment, the elongate member can have at least one intermediate configuration between said first and second configurations.

In a still further embodiment shown in FIG. 5, at least a portion of the outer surface can have a coating of lubricious material 57. In a further embodiment, a substantial portion of the outer surface can have a coating of the lubricious material 57. In a still further embodiment, the entire outer surface of the elongate member can have a coating of the lubricious material 57.

The lubricious material 57 preferably becomes lubricious on being brought into contact with a fluid, such as a saline solution. Still further, the coating 57 preferably becomes lubricious on being brought into contact with a body fluid, such as cochlear fluid.

In one embodiment, the lubricious material 57 is selected from the group comprising polyacrylic acid (PAA), polyvinyl alcohol (PVA), polylactic acid (PLA) and polyglycolic acid (PGA). It is envisaged that other similar materials could also be used. It is envisaged that the lubricious material 57 can also be impregnated with the bio-active substance allowing the coating to perform a dual role. The rate of delivery of the bio-active substance can be programmed by design of the coating structure.

In yet another embodiment, the device can include a stiffening element made of a second material relatively stiffer than the resiliently flexible material of the elongate member. The stiffening element can be adapted to bias the elongate member into the first configuration.

In a still further embodiment, the device can include a stiffening sheath that envelops said elongate member and which is made of a material that is relatively stiffer than the resiliently flexible material of the elongate member. The stiffening sheath can be adapted to bias the elongate member into the first configuration. In one embodiment, the stiffening sheath can be overlaid by the coating of lubricious material.

Where both the stiffening element and stiffening sheath are present in the device, the element and sheath can be adapted in combination to bias said elongate member into said first configuration. In this embodiment, if either the stiffening element or the stiffening sheath is removed or deactivated, the elongate member can adopt said at least one intermediate configuration. In this embodiment, the stiffening sheath can be formed of the same material or a different material to that of the stiffening element. In either case, the stiffening sheath can be relatively more stiffer or relatively less stiffer than the stiffening element.

In a preferred embodiment, the second configuration of the elongate member is curved. More preferably, the elongate member adopts a spiral configuration when in the second configuration.

The elongate member is preferably preformed from a plastics material with memory and is preformed to the second configuration.

In a preferred embodiment, the first configuration is preferably substantially straight. More preferably, the first configuration is straight.

In a preferred embodiment, the elongate member is formed from a suitable biocompatible material. In one embodiment, the material can be a silicone, such as Silastic MDX 4-4210. In another embodiment, the elongate member can be formed from a polyurethane or similar material.

In one embodiment, the stiffening element is formed of a bioresorbable material which softens or dissolves on exposure to a fluid. The stiffening element can soften or dissolve on exposure to a saline solution or a body fluid of the implantee, such as cochlear fluid.

In a further embodiment, the bioresorbable material of the stiffening element is selected from the group comprising polyacrylic acid (PAA), polyvinyl alcohol (PVA), polylactic acid (PLA) and polyglycolic acid (PGA). It is envisaged that other similar materials could also be used. It is envisaged that the bioresorbable material of the stiffening element can also be impregnated with one or more of the bio-active substances allowing the stiffening element to perform a dual role. The rate of delivery of the bio-active substance can be determined by the structural design of, or the materials used in, the stiffening element structure.

In another embodiment, the stiffening element can be formed from a non-bioresorbable material. In this embodiment, the stiffening element can comprise a metallic stylet, or a stylet-like element formed from any other suitable stiffening material, extending through a lumen in the elongate member. In one embodiment, the wire can be formed from a biocompatible metal, a biocompatible metallic alloy or a biocompatible relatively stiff plastic. In a preferred embodiment, a metal stylet can be formed from platinum.

In a still further embodiment, the stiffening element can be formed from a shape memory or heat sensitive material. For example, the stiffening element can be formed from a bimetallic element (such as nickel/titanium) and shaped to take a straight or substantially straight configuration at room temperature but bend into another shape on exposure to body temperature (eg. about 37° C.).

The lumen for the stylet can be the same lumen as utilised in one embodiment of the substance delivery means defined above. In another embodiment, the lumen can be a different lumen to that utilised as part of the substance delivery means defined above. The lumen for the stylet can be cylindrical and also can have an opening formed therein. In the case of a metal stylet, the stylet can extend out of the opening allowing the stylet to be manipulated and removed from the lumen during or following insertion of the device. In the case of a bioresorbable stiffening element, the opening can act as a fluid ingress means allowing body fluids to enter the lumen on insertion of the device into an implantee.

The stiffening sheath, if present, can be formed of a bioresorbable material which dissolves or softens on exposure to a fluid. The stiffening sheath can dissolve or soften on exposure to a saline solution or a body fluid of the implantee, such as cochlear fluid and in doing so also release one or more bio-active substances impregnated therein.

In a further embodiment, the bioresorbable material of the stiffening sheath is selected from the group comprising polyacrylic acid (PAA), polyvinyl alcohol (PVA), polylactic acid (PLA) and polyglycolic acid (PGA). It is envisaged that other suitable materials could also be used. It is envisaged that the bioresorbable element of the stiffening sheath can also be impregnated with one or more bio-active substances allowing the stiffening sheath to perform a dual role. The rate of delivery of the bio-active substance can be set by the structural design of, or the materials used in, the sheath structure.

The device can include an additional layer surrounding the stiffening sheath. The additional layer can have a first rate of fluid ingress therethrough and have at least one fluid ingress means formed therein, the rate of fluid ingress through the fluid ingress means being greater than the first rate of fluid ingress through the additional layer. In this embodiment, the coating of lubricious material can be coated on the outside of the additional layer.

The fluid ingress means can comprise one or more openings in the additional layer. The openings can be closable. The openings can comprise slits in the additional layer. The slits can be formed to allow substantially the same or the same rate of ingress of fluid through the additional layer. In another embodiment, at least one slit can allow a different rate of progress of fluid through the additional layer compared to the other slits. In one embodiment, the slits can be sealable with a bioresorbable material. The bioresorbable material preferably softens and/or dissolves on exposure to a fluid, such as cochlear fluid, to allow ingress of the fluid into the elongate member. In this embodiment, the slits can be sealed with the same or a different quantity and/or the same or different thicknesses of bioresorbable material. Variations in thickness and/or quantity of the bioresorbable material provide a means of varying the rate of ultimate dissolution of the stiffening element of the device, if present, and/or the rate of elution of said at least one bioactive substance.

In another embodiment, the slits can be designed so that when the electrode array is in a straight configuration the slits are closed, preventing the ingress of fluid therethrough. The closure of the slits can be formed by the material of the outer wall, such as silicone, being under compression. When the electrode array is inserted into the cochlea and begins to assume a curved configuration, the slits become open allowing the ingress of fluid therethrough, due in the main to the silicone in the outer wall being released from the state of compression. Such a design allows greater control of the rate of fluid ingress and subsequent dissolution of the stiffening element of the device and/or the elution of said at least one bioactive substance.

The stiffening sheath, if present, can be formed from a shape memory or heat sensitive material. For example, the stiffening sheath can be formed from a bimetallic or alloy filament (such as nickel/titanium) and shaped to take and maintain the straight or substantially straight configuration of the elongate member at room temperature but bend it into another shape once it is exposed to body temperature.

In one embodiment, while both the stiffening element and the stiffening sheath are in position within the device, it will retain the first configuration, which as discussed is preferably straight. If the stiffening sheath is removed or softened, whether it is by dissolution or otherwise, the remaining stiffening element can have insufficient strength to retain the elongate member in its first configuration. It is preferred that the elongate member, on removal or softening of the stiffening sheath, will adopt an intermediate configuration in which the elongate member has at least some curvature.

The present invention provides a surgeon with a cochlear implant electrode array that can assist with the delivery of one or more bio-active substances to the implantation site following its implantation. The substances that can be delivered by the present device include substances that are adapted to promote healing, substances that prevent bleeding or at least excessive bleeding, and also substances that prevent the growth of tissue, including scar tissue, in the cochlea following implantation. Pharmaceutical compounds such as anti-inflammatories and antibiotics can also be delivered by the present device.

It is also envisaged that substances that assist in reducing the resting potential of the surrounding neurons can also be delivered by the present invention. It should be appreciated that during neural stimulation the neurons propagate an action potential through the response of transmembrane ion channels to local electrical fields. By delivering a substance that elicits a change in the transmembrane potential, the resting neural membrane potential can be moved towards the activation potential resulting in a lowering of the energy required to be delivered to activate the neuron. This also has the potential to reduce the power required by the stimulation device as well as increase the specificity of the electrical stimulation and restore the stochastic response of the neurons.

In one embodiment, and where the elongate member is impregnated with a bio-active substance, the device can be formed by a method that includes a step of impregnating the elongate member with the bio-active substance prior to implantation. Impregnation may be achieved by soaking the elongate member in a solution that constitutes or includes the bio-active substance for a period of time. The degree of impregnation can be controlled by the period of time of soaking of the elongate member. It is anticipated that the degree of impregnation will impact on the rate of substance delivery by the device following implantation.

In another embodiment, and where the elongate member includes a lumen acting as a reservoir for a bio-active substance, the lumen can be filled with the bio-active substance prior to implantation. In one embodiment, the lumen can be filled during manufacture and/or packaging of the elongate member. In another embodiment, the lumen can be filled, such as by the surgeon, just prior to implantation. The substance egress means preferably does not allow the bio-active substance to pass from the lumen until the device is ready for implantation or after implantation. In one embodiment, the substance egress means could be activated by the surgeon just prior to its insertion into the implantee. In another embodiment, the substance egress means may be coated with a layer of bioresorbable material that softens and/or dissolves on exposure to a fluid, such as cochlear fluid. Following its dissolution, the bio-active substance is free to pass through the substance egress means.

The device can be adapted to only provide delivery of a bio-active substance to the implantation site for a particular period following implantation. This period may comprise any period of time from a few hours or days to a few weeks or even months. In another embodiment, the device can be used as a means of delivery of bio-active substances to the implantee well beyond the time of implantation. For example, the additional reservoir can be periodically filled with a bio-active substance to ensure continued supply of the bio-active substance to the implantation site. The additional reservoir, in this case, may be positioned beneath but adjacent the surface of the skin of the implantee thereby allowing the reservoir to be filled by a syringe and needle assembly that injects the bio-active substance into the additional reservoir.

Once implanted, the electrodes can receive stimulation signals from a stimulator means. The stimulator means is preferably electrically connected to the elongate member by way of an electrical lead. The lead can include the one or more wires extending from each electrode of the array mounted on the elongate member.

In one embodiment, the lead can extend from the elongate member to a stimulator means or at least the housing thereof. In one embodiment, the lead is continuous with no electrical connectors, at least external the housing of the stimulator means, required to connect the wires extending from the electrodes to the stimulator means. One advantage of this arrangement is that there is no requirement for the surgeon implanting the device to make the necessary electrical connection between the wires extending from the electrodes and the stimulator means.

The stimulator means is preferably positioned within a housing that is implantable within the implantee. The housing for the stimulator means is preferably implantable within the bony well in the bone behind the ear posterior to the mastoid.

When implantable, the housing preferably contains, in addition to the stimulator means, a receiver means. The receiver means is preferably adapted to receive signals from a controller means. The controller means is, in use, preferably mounted external to the body of the implantee such that the signals are transmitted transcutaneously through the implantee.

Signals can preferably travel from the controller means to the receiver means and vice versa. The receiver means can include a receiver coil adapted to receive radio frequency (RF) signals from a corresponding transmitter coil worn externally of the body. The radio frequency signals can comprise frequency modulated (FM) signals. While described as a receiver coil, the receiver coil can preferably transmit signals to the transmitter coil which receives the signals.

The transmitter coil is preferably held in position adjacent the implanted location of the receiver coil by way of respective attractive magnets mounted centrally in, or at some other position relative to, the coils.

The external controller can comprise a speech processor adapted to receive signals output by a microphone. During use, the microphone is preferably worn on the pinna of the implantee, however, other suitable locations can be envisaged, such as a lapel of the implantee's clothing. The speech processor encodes the sound detected by the microphone into a sequence of electrical stimuli following given algorithms, such as algorithms already developed for cochlear implant systems. The encoded sequence is transferred to the implanted stimulator/receiver means using the transmitter and receiver coils. The implanted stimulator/receiver means demodulates the FM signals and allocates the electrical pulses to the appropriate attached electrode by an algorithm which is consistent with the chosen speech coding strategy.

The external controller further comprises a power supply. The power supply can comprise one or more rechargeable batteries. The transmitter and receiver coils are used to provide power via transcutaneous induction to the implanted stimulator/receiver means and the electrode array.

While the implant system can rely on external componentry, in another embodiment, the controller means, including the microphone, speech processor and power supply can also be implantable. In this embodiment, the controller means can be contained within a hermetically sealed housing or the housing used for the stimulator means.

BRIEF DESCRIPTION OF THE DRAWINGS

By way of example only, a preferred embodiment of the invention is now described with reference to the accompanying drawings, in which.

PREFERRED MODE OF CARRYING OUT THE INVENTION

Figure 1:
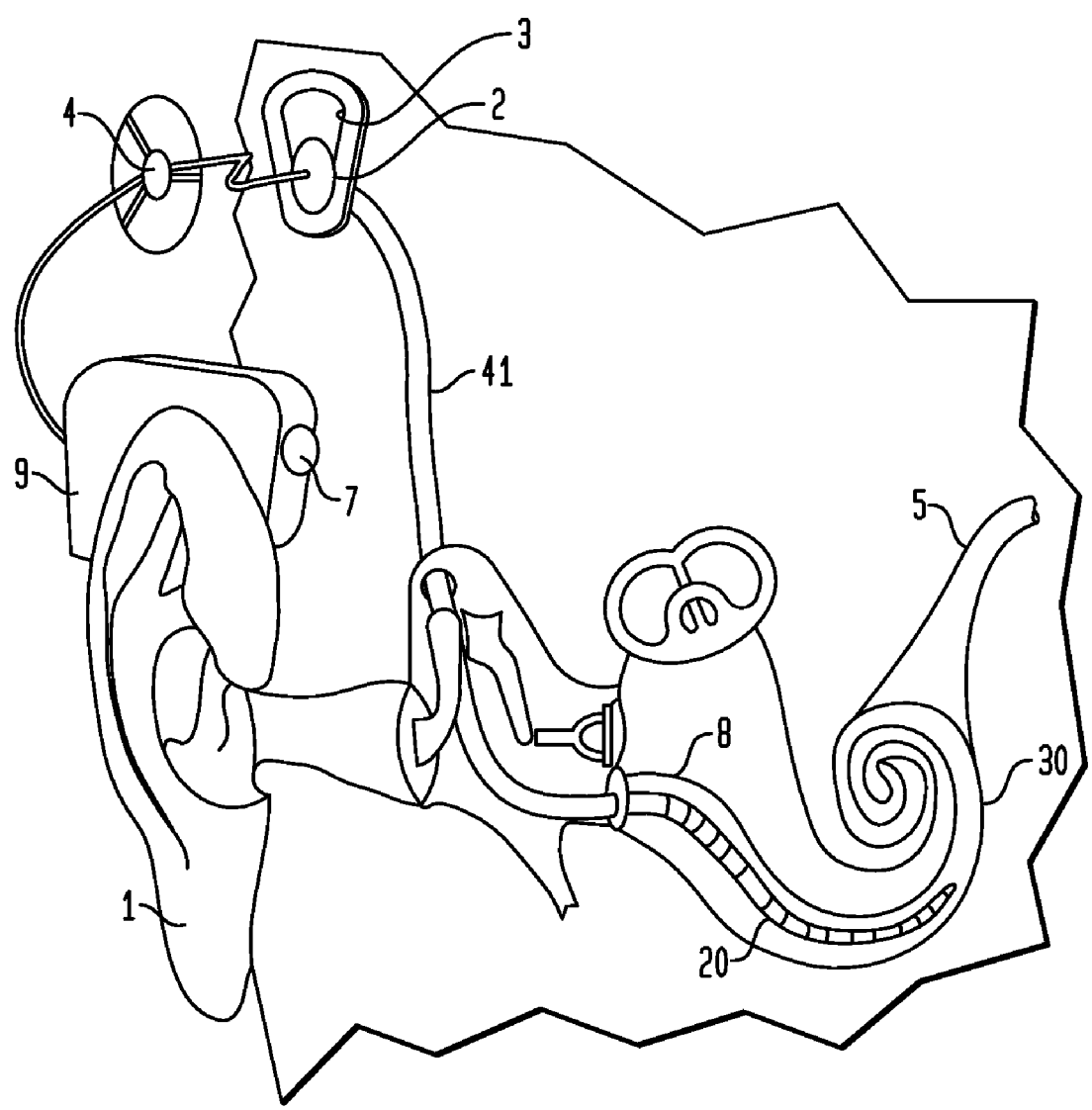
FIG. 1 is a pictorial representation of a prior art cochlear implant system.

Before describing the features of the present invention, it is appropriate to briefly describe the construction of one type of known cochlear implant system with reference to FIG. 1.

Known cochlear implants typically consist of two main components, an external component including a speech processor 9, and an internal component including an implanted receiver and stimulator unit 2. The external component includes a microphone 7. The speech processor 9 is, in this illustration, constructed and arranged so that it can fit behind the outer ear 1. Alternative versions may be worn on the body. Attached to the speech processor 9 is a transmitter coil 4 which transmits electrical signals to the implanted unit 2 via a radio frequency (RF) link.

The implanted component includes a receiver coil 3 for receiving power and data from the transmitter coil 4. A cable 41 extends from the implanted receiver and stimulator unit 2 to the cochlea 30 and terminates in an electrode array 20. The signals thus received are applied by the array 20 to the basilar membrane 8 and the nerve cells within the cochlea 30 thereby stimulating an auditory nerve 5. The operation of such a device is described, for example, in U.S. Pat. No. 4,532,930.

Figure 2:
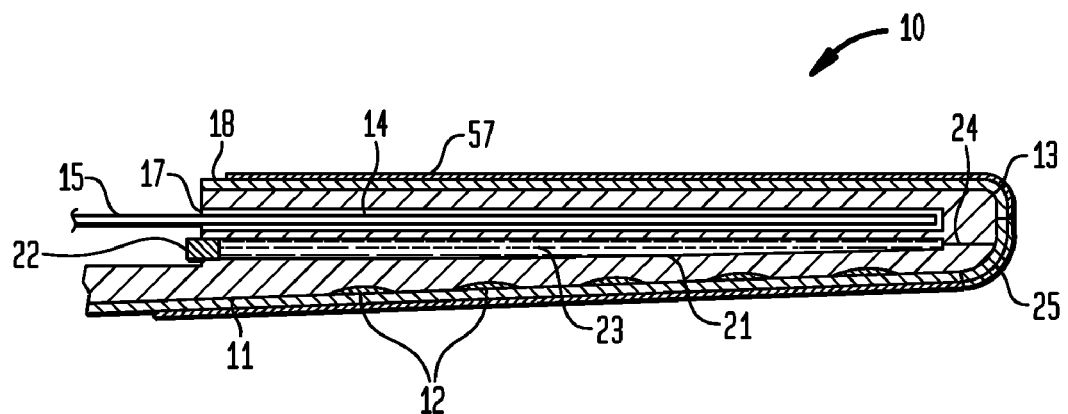
FIG. 2 is a simplified cross-sectional view of one embodiment of an electrode assembly according to the present invention ready for insertion into a cochlea.
Figure 3:
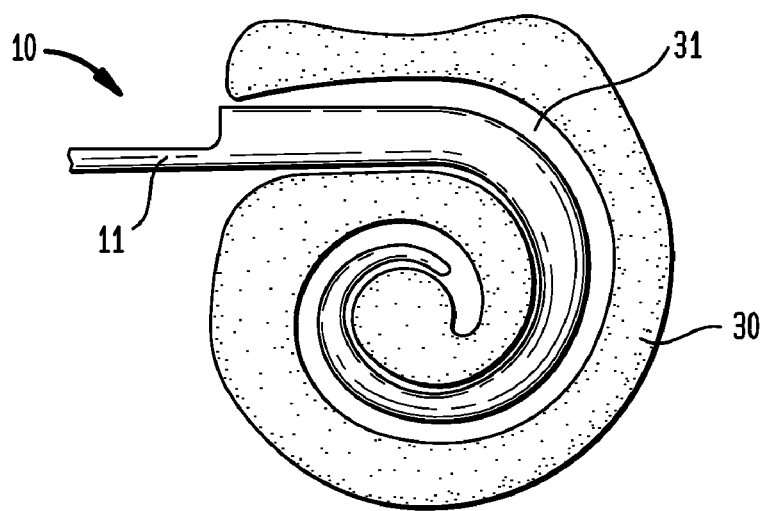
FIG. 3 is a simplified part-sectional, part side elevational view of the electrode assembly depicted following insertion in the cochlea.

One embodiment of a cochlear implant electrode assembly according to the present invention is depicted generally as 10 in FIGS. 2 and 3.

The depicted electrode assembly 10 has an electrical lead extending back to a stimulator/receiver housing, such as the stimulator unit 2 depicted in FIG. 1. In considering this invention, it is to be understood that each electrode 12 may have one or more wires (not depicted) electrically connected thereto and extending from each respective electrode 19 back through the lead to the stimulator/receiver.

The assembly 10 comprises an elongate electrode carrier member 11 having a plurality of electrodes 12 mounted thereon. For the purposes of clarity, the electrodes 12 depicted in FIG. 1 are not necessarily shown to scale. A larger number of electrodes than that depicted in FIG. 2 can also be envisaged. The electrodes 12 are not depicted in FIG. 3 for reasons of clarity.

The depicted elongate member 11 is preformed from a resiliently flexible silicone with memory and is preformed to a curved configuration suitable for insertion in the scala tympani 31 of a human cochlea 30. While an assembly that normally adopts a curved configuration when in a relaxed condition is depicted in the drawings, it will be appreciated that the present invention also could be utilised with respect to assemblies that are normally straight when in a relaxed condition.

The elongate member 11 has a first end 13 that is firstly inserted into the cochlea 30 upon insertion of the assembly 10.

As depicted in FIG. 2, there is disposed within a lumen 14, prior to insertion of the assembly 10 into the cochlea 30, a substantially straight platinum stylet 15. In the depicted embodiment, the stylet 15 has a stiffness that is sufficient to retain the silicone elongate member 11 in a straight configuration. The stylet could be constructed so as to have a stiffness that was insufficient alone to retain the elongate member 11 in a straight configuration. In this case, the elongate member could have a stiffening sheath 18 that at lest partially envelops the elongate member 11. The stiffening sheath 18 could be formed of a bioresorbable material which prior to implantation assists the platinum stylet in maintaining the elongate member 11 in the straight configuration.

While a platinum stylet is depicted, a bioresorbable stylet-like member formed from a bioresorbable material, such as polyacrylic acid (PAA), that is also impregnated with a bioactive substance and which is adapted to dissolve or soften on exposure to cochlear fluids, could be utilised with appropriate modification to the elongate carrier member 11. A stiffening polymer stylet could also be utilised which could be impregnated with a bio-active substance. Such a stylet would soften quickly, but not dissolve quickly, with its very slow dissolution rate allowing the drug to effectively elute to the body. Equally, whilst a substantially cylindrical lumen is depicted, the lumen 14 could indeed be any shape necessary to perform the function. Again, the PAA stylet-like member in this invention can have a stiffness that is either sufficient or insufficient to retain the silicone elongate member 11 in a straight configuration as depicted in FIG. 2. It will be appreciated that a bioresorbable stylet-like member could be formed from other suitable bioresorbable materials. A stylet-like member made from a shape memory or heat sensitive material could also be utilised instead of stylet 15.

In the depicted embodiment, the elongate member 11 is adapted to also act as a system for delivery of one or more pharmaceutical or bioactive substances to the cochlea 30. In the depicted embodiment, this system is provided by an additional lumen 21 that acts as a reservoir for a fluid 23 constituting or including the one or more pharmaceutical or bioactive substances. The lumen 21 is pre-filled with the pharmaceutical or bioactive substances during manufacture and then sealed by the plug closure 22.

Provided at the first end 13 of the member 11 is a fluid egress means comprising a valve 24 in the form of a slit formed in the structure of the elongate member 11. Other embodiments with more than one slit 24 can be envisaged. The slit 24 is adapted to allow fluid 23 within the lumen 21 to exit the lumen 21 but prevents fluid flow from external the member 11 back into the lumen 21. To prevent flow of fluid through the slit 24 prior to implantation, the slit is covered with a layer 25 of bioresorbable PAA. Other suitable bioresorbable materials could be envisaged and the material could also be impregnated with the pharmaceutical substance. While only depicted as covering the slit 24, the layer 25 could coat a greater portion or the entire surface of the elongate member 11.

On insertion of the elongate member 11 into the scala tympani 31, the cochlear fluid commences to soften and dissolve the layer 25 of PAA. In addition to lubricating the first end 13, the dissolution of the layer 25 allows the fluid 23 to commence to flow from the lumen 21 into the scala tympani 31.

Figure 6A:
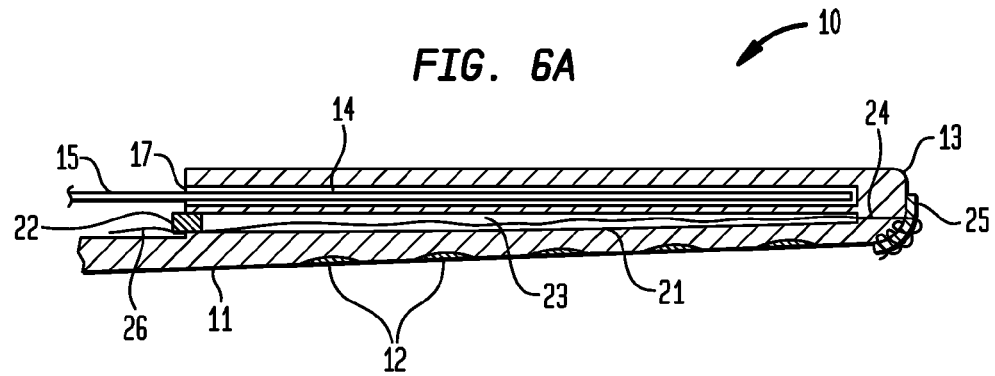
FIG. 6 is a simplified cross-sectional view of an electrode assembly in accordance with another embodiment of the present invention.
Figure 6B:
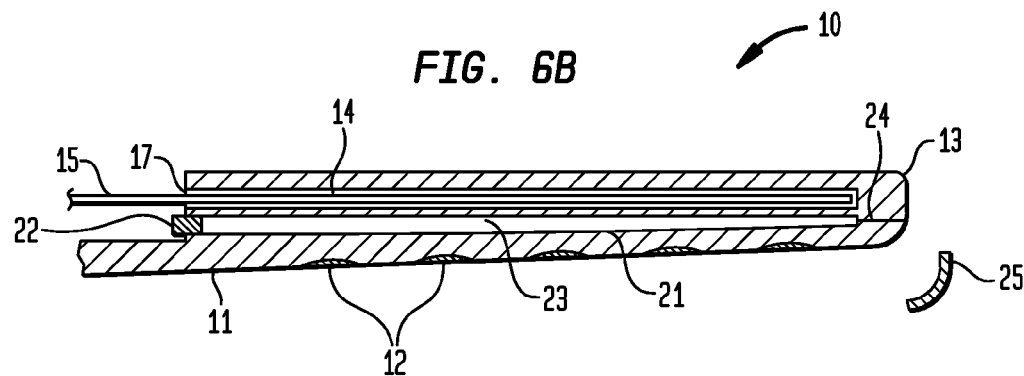

It is also possible that the pharmaceutical or bioactive substance 23 could be released from the lumen 21 by way of a mechanical means. Such a means may include pushing the stylet 15 through the slit 24 at the end of the assembly 10 to break the seal just prior to insertion. As shown in FIGS. 6A and 6B, another method of releasing the pharmaceutical substance would be to include a suture 26 down the lumen 21 and through the seal 25 (FIG. 6A). The suture 26 could then be pulled in an action similar to a "rip-cord" to open the end of the assembly 10 (FIG. 6B).

Figure 4:
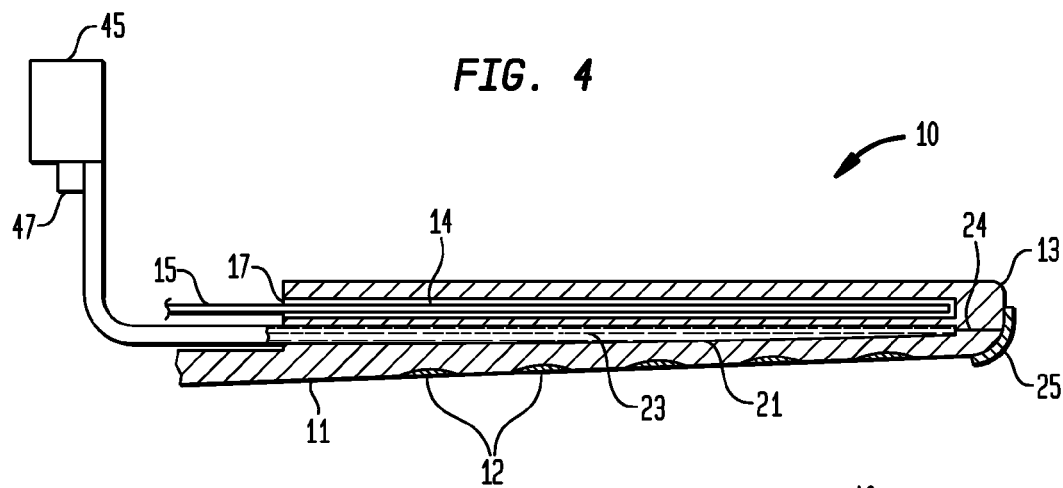
FIG. 4 is a simplified cross-sectional view of an electrode assembly in accordance with another embodiment of the present invention.
Figure 5:
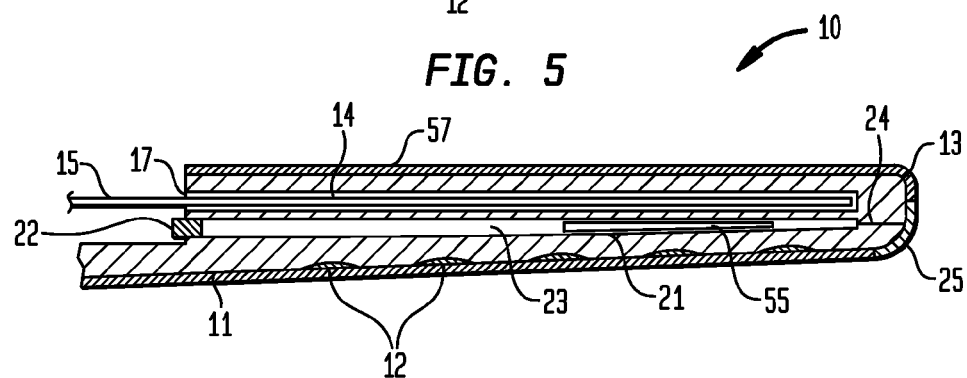
FIG. 5 is a simplified cross-sectional view of an electrode assembly in accordance with a still further embodiment of the present invention.

In the embodiments shown in FIG. 4, lumen 21 is in fluid communication with an additional reservoir 45 for fluid 23. Additional reservoir 45 can be placed under the skin of the implantee and be fillable by a needle and syringe assembly when required. A pump 47, such as an osmotic pump, can be used to transfer fluid from additional reservoir 45 to lumen 21.

While depicted with a lumen 21, it can also be envisaged that the elongate member 11 could be impregnated with a pharmaceutical agent or other bioactive substance prior to implantation. The pharmaceutical agent or bioactive substance would then be free to leach from the elongate member 11 following insertion. In this embodiment, it can be envisaged that a layer of bioresorbable PAA material may coat the entire impregnated portion of the elongate member 11 so ensuring that the pharmaceutical agent or bioactive substance does not leach from the elongate member 11 prior to implantation.

While the elongate member 11 is manufactured with a preformed curved configuration, the depicted assembly 10 is typically delivered to a surgeon in a sterile package with the stylet 15 and pharmaceutical fluid 23 in place (as depicted in FIG. 2).

On removal from the package and insertion into the scala tympani 31 of the cochlea 30, the cochlear fluids commence to dissolve and soften the layer 25.

As the elongate member 11 is inserted into the scala tympani 31 of the cochlea 30, the surgeon can commence to withdraw the stylet 15 from the lumen 14 through opening 17. On withdrawal of the stylet 15, the elongate member 11 is free to adopt the spiral configuration depicted in FIG. 3 with the electrodes 12 facing the modiola within the cochlea 30 so that they are positioned as close as possible to the spiral ganglia thereof.

The provision of a system for delivering a pharmaceutical substance that promotes healing and/or more efficient neural stimulation while preventing the formation of substantial scar tissue in the cochlea, enhances the likelihood of successful long-term placement of the assembly 10 in the cochlea and subsequent successful use of the cochlear implant by the implantee.

While the preferred embodiment of the invention has been described in conjunction with a cochlear implant, it is to be understood that the present invention has wider application to other implantable electrodes, such as electrodes used with pacemakers.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A cochlear implant electrode assembly device comprising:
   a resiliently flexible elongate member having disposed therein a sealable reservoir configured to receive a bioactive substance;
   a plurality of electrodes mounted on said elongate member configured to provide stimulation to a cochlea; and
   a substance egress fluidically coupling said reservoir to the exterior of said elongate member, wherein said substance egress is configured to release said bio-active substance from said reservoir following implantation of said device, wherein said substance egress comprises an opening in said reservoir sealed with a layer of bioresorbable material configured to dissolve following implantation of said device,
   a stiffening member configured to bias said elongate member into a first configuration, and wherein said elongate member adopts a second configuration upon deactivation or removal of said stiffening member, wherein said stiffening member comprises a stiffening element extending through a lumen in said elongate member, said stiffening element made of a material relatively stiffer than said resiliently flexible material of said elongate member, and formed of a bioresorbable material which softens or dissolves on exposure to a cochlear fluid.

2. The device of claim 1, wherein said bioresorbable material of said stiffening element is selected from the group comprising polyacrylic acid (PAA), polyvinyl alcohol (PVA), polylactic acid (PLA) and polyglycolic acid (PGA).

3. The device of claim 1, wherein said bioresorbable material of said stiffening element is impregnated with one or more said bio-active substances.

4. A cochlear implant electrode assembly device comprising:
   a resiliently flexible elongate member having disposed therein a sealable reservoir adapted to receive a bio-active substance;
   a plurality of electrodes mounted on said elongate member configured to provide stimulation to a cochlea; and
   a substance egress fluidically coupling said reservoir to the exterior of said elongate member, wherein said substance egress is configured to release said bio-active substance from said reservoir following implantation of said device, wherein said substance egress comprises:
      a seal disposed at an opening in said reservoir to seal said reservoir; and
      a suture through said reservoir and said seal, wherein at least partial removal of said suture at least partially opens said reservoir.

5. The device of claim 4, wherein said elongate member is impregnated with at least one bio-active substance that can leach from said elongate member following implantation.

6. The device of claim 5, wherein said device further comprises a closure configured to sealably close an opening of said lumen.

7. The device of claim 6, wherein said closure comprises a plug insertable in said lumen to form a seal therewith.

8. The device of claim 7, wherein said plug is formed from a resiliently flexible material selected from the group comprising a silicone and a polyurethane.

9. The device of claim 4, wherein said reservoir comprises a lumen extending through at least a portion of the length of said elongate member.

10. The device of claim 4, wherein said bio-active substance is carried in or comprises a fluid, and said at least one substance egress is a fluid egress.

11. The device of claim 10, wherein each said at least one fluid egress comprises a valve configured to allow a fluid to exit said elongate member and to substantially prevent fluid flow from external said elongate member into said elongate member.

12. The device of claim 4, further comprising an additional reservoir external to said elongate member in fluid communication with said reservoir.

13. The device of claim 12, further comprising a pump configured to transfer said bio-active substance from said additional reservoir into said reservoir for subsequent delivery to a site of implantation of said elongate member.

14. The device of claim 4, further comprising a ceramic or polymer pellet impregnated with said bio-active substance, wherein said pellet is disposed in said reservoir and is configured to release said bio-active substance at a desired rate.

15. The device of claim 4, wherein said bio-active substance comprises a steroid.

16. The device of claim 4, wherein said bio-active substance is configured to reduce the resting neuron potential of neurons within the cochlea.

17. The device of claim 4, further comprising a stiffening member configured to bias said elongate member into a first configuration, and wherein said elongate member adopts a second configuration upon deactivation or removal of said stiffening member in order to apply a desired tissue stimulation.

18. The device of claim 17, wherein said elongate member is configured to adopt at least one intermediate configuration between said first and second configurations.

19. The device of claim 17, wherein said stiffening member comprises:
   a stiffening sheath that at least partially envelops said elongate member, said sheath made of a material that is relatively stiffer than said resiliently flexible material of said elongate member.

20. The device of claim 19, wherein said stiffening sheath further comprises a coating of a lubricious material partially overlaying said stiffening sheath.

21. The device of claim 17, wherein said second configuration of said elongate member is curved.

22. The device of claim 21, wherein said second configuration of said elongate member is a spiral configuration.

23. The device of claim 17, wherein said first configuration is at least substantially straight.

24. The device of claim 17, wherein said stiffening member comprises:
   a stiffening element extending through a lumen in said elongate member, said stiffening element made of a material relatively stiffer than said resiliently flexible material of said elongate member, and formed of a bioresorbable material which softens or dissolves on exposure to a cochlear fluid.

25. The device of claim 24, wherein said bioresorbable material of said stiffening element is selected from the group comprising polyacrylic acid (PAA), polyvinyl alcohol (PVA), polylactic acid (PLA) and polyglycolic acid (PGA).

26. The device of claim 24, wherein said bioresorbable material of said stiffening element is impregnated with one or more said bio-active substances.

27. The device of claim 17, wherein said stiffening member comprises:
   a stiffening element extending through a lumen in said elongate member, said stiffening element made of a material relatively stiffer than said resiliently flexible material of said elongate member, and formed of a non bioresorbable material selected from the group comprising a metallic stylet and a non metallic stylet.

28. The device of claim 4, wherein said elongate member further comprises a coating of lubricious material on at least a portion of the outer surface of said elongate member.

29. The device of claim 28, wherein said lubricious material is selected from the group comprising polyacrylic acid (PAA), polyvinyl alcohol (PVA), polylactic acid (PLA) and polyglycolic acid (PGA).

30. The device of claim 28, wherein said lubricious material is impregnated with said bio-active substance.

31. The device of claim 4, wherein said elongate member is formed from a biocompatible material selected from the group comprising a silicone and a polyurethane.

32. The device of claim 4, wherein said device is configured to deliver said bio-active substance to a site of implantation of said elongate member for a desired period of time following implantation.

33. A cochlear implant electrode assembly device comprising:
   a resiliently flexible elongate member having disposed therein a sealable reservoir adapted to receive a bio-active substance;

a plurality of electrodes mounted on said elongate member configured to provide stimulation to a cochlea;

a substance egress fluidically coupling said reservoir to the exterior of said elongate member, wherein said substance egress is configured to release said bio-active substance from said reservoir following implantation of said device, wherein said substance egress comprises a sealed opening, wherein said elongate member further comprises a coating of lubricious material on at least a portion of the outer surface of said elongate member; and a stylet configured to puncture said sealed opening of said substance egress prior to insertion of said device.

34. The device of claim 33, wherein said lubricious material is selected from the group comprising polyacrylic acid (PAA), polyvinyl alcohol (PVA), polylactic acid (PLA) and polyglycolic acid (PGA).

35. The device of claim 33, wherein said lubricious material is impregnated with said bio-active substance.

36. The device of claim 33, further comprising a stiffening member configured to bias said elongate member into a first configuration, and wherein said elongate member adopts a second configuration upon deactivation or removal of said stiffening member in order to apply a desired tissue stimulation, wherein said stiffening member comprises:

a stiffening sheath that at least partially envelops said elongate member, said sheath made of a material that is relatively stiffer than said resiliently flexible material of said elongate member.

37. The device of claim 36, wherein said stiffening sheath further comprises a coating of a lubricious material partially overlaying said stiffening sheath.

38. A cochlear implant electrode assembly device comprising:

a resiliently flexible elongate member having disposed therein a sealable reservoir adapted to receive a bio-active substance;

a plurality of electrodes mounted on said elongate member configured to provide stimulation to a cochlea; and a substance egress fluidically coupling said reservoir to the exterior of said elongate member, wherein said substance egress is configured to release said bio-active substance from said reservoir following implantation of said device, wherein said substance egress comprises: a sealed opening configured to be punctured by a stylet prior to insertion of said device, a stiffening member configured to bias said elongate member into a first configuration, and wherein said elongate member adopts a second configuration upon deactivation or removal of said stiffening member in order to apply a desired tissue stimulation, wherein said stiffening member comprises a stiffening element extending through a lumen in said elongate member, said stiffening element made of a material relatively stiffer than said resiliently flexible material of said elongate member, and formed of a bioresorbable material which softens or dissolves on exposure to a cochlear fluid.

39. The device of claim 38, wherein said bioresorbable material of said stiffening element is selected from the group comprising polyacrylic acid (PAA), polyvinyl alcohol (PVA), polylactic acid (PLA) and polyglycolic acid (PGA).

40. The device of claim 38, wherein said bioresorbable material of said stiffening element is impregnated with one or more said bio-active substances.

* * * * *